US007357939B2

(12) United States Patent
Bessette

(10) Patent No.: US 7,357,939 B2
(45) Date of Patent: Apr. 15, 2008

(54) SYNERGISTIC AND RESIDUAL PESTICIDAL COMPOSITIONS CONTAINING PLANT ESSENTIAL OILS WITH ENZYME INHIBITORS

(75) Inventor: Steven M. Bessette, Brentwood, TN (US)

(73) Assignee: Ecosmart Technologies, Inc., Alpharetta, GA (US)

( * ) Notice: Subject to any disclaimer, the term of this patent is extended or adjusted under 35 U.S.C. 154(b) by 0 days.

(21) Appl. No.: 11/261,596

(22) Filed: Oct. 31, 2005

(65) Prior Publication Data
US 2006/0121074 A1 Jun. 8, 2006

Related U.S. Application Data

(62) Division of application No. 09/340,391, filed on Jun. 28, 1999, now Pat. No. 6,986,898.

(51) Int. Cl.
A01N 25/32 (2006.01)

(52) U.S. Cl. ............... 424/406; 424/405; 514/464; 514/546

(58) Field of Classification Search ............... None
See application file for complete search history.

(56) References Cited

U.S. PATENT DOCUMENTS

| 4,195,080 | A | | 3/1980 | Herrera et al. | |
|---|---|---|---|---|---|
| 4,368,207 | A | | 1/1983 | Lover et al. | |
| 6,004,569 | A | | 12/1999 | Bessette et al. | |
| 6,114,384 | A | * | 9/2000 | Bessette et al. | 514/546 |
| 6,124,275 | A | * | 9/2000 | Emerson | 514/159 |
| 6,849,614 | B1 | * | 2/2005 | Bessette et al. | 514/72 |
| 6,887,899 | B1 | * | 5/2005 | Bessette | 514/546 |
| 6,986,898 | B1 | * | 1/2006 | Bessette | 424/406 |

FOREIGN PATENT DOCUMENTS

| BE | 1002598 A | 4/1991 |
|---|---|---|
| CA | 2099929 A | 1/1994 |
| CA | 2077284 A | 3/1994 |
| DE | 3526911 A | 3/1986 |
| DE | 3717467 A | 12/1988 |
| DE | 3733640 A | 4/1989 |
| WO | WO 98/49901 A | 11/1998 |
| WO | WO 98/54971 A | 12/1998 |

OTHER PUBLICATIONS

Metcalf/Flint Destructive & Useful Insects p. 186,, 1962.*
Ngoh, S.P., et al., "Insecticidal and Repellant Properties of Nine Volatile Constituents of Essential Oils Against the American Cockroach, Periplaneta Americana (L.)", *Pesticide* Science, 54(3) (1998) whole document.
Singh, K. et al., "Synergism of MGK-264 and piperonyl butoxide on the toxicity of plant derived molluscicides", *Chemosphere*, 36(15):3055-3060 (Database, CHEMABS 'Online!, Chemical Abstracts Service, Columbus, OH,).
Casida, PYRETHRUM, pp. 25-27, 30-31, 86-91, 196-199, 202-203, 232-233, 267 & 276 (1973).

* cited by examiner

*Primary Examiner*—Neil S. Levy
(74) *Attorney, Agent, or Firm*—Nixon & Vanderhye P.C.

(57) ABSTRACT

Synergistic and residual pesticidal compositions containing synergistic and residual mixtures of plant essential oils in admixture with enzyme inhibitors, with or without other compounds not previously used as active ingredients in pesticidal formulations. In addition, the present invention is directed to a method for controlling pests by applying a pesticidally-effective amount of the above synergistic and residual pesticidal compositions to a locus where pest control is desired.

5 Claims, No Drawings

SYNERGISTIC AND RESIDUAL PESTICIDAL COMPOSITIONS CONTAINING PLANT ESSENTIAL OILS WITH ENZYME INHIBITORS

CROSS-REFERENCES TO RELATED APPLICATIONS

This application is a divisional of U.S. application Ser. No. 09/340,391, filed Jun. 28, 1999 now U.S. Pat. No. 6,986,898, the entire disclosure of which is incorporated herein by reference.

FIELD OF THE INVENTION

The present invention relates, in general, to synergistic and residual pesticidal compositions containing plant essential oils and/or derivatives thereof with enzyme inhibitors. In one aspect, the present invention relates to synergistic pesticidal compositions containing one or more plant essential oils and/or derivatives thereof in admixture with enzyme inhibitors. In another aspect, the present invention relates to residual pesticidal compositions containing one or more plant essential oils and/or derivatives thereof in admixture with enzyme inhibitors. In still another aspect, the present invention relates to synergistic and residual pesticidal compositions containing one or more plant essential oils and/or derivatives thereof in admixture with enzyme inhibitors and other synergists. In a further aspect, the present invention relates to a method for controlling pests by the application of pesticidally effective amounts of the synergistic and residual pesticidal compositions to a locus where pest control is desired.

BACKGROUND OF THE INVENTION

Pests (invertebrates, insects, arachnids, larvae thereof, etc.) are annoying to humans for a myriad of reasons. They have annually cost humans billions of dollars in crop losses and in the expense of keeping them under control. For example, the losses caused by pests in agricultural environments include decreased crop yield, reduced crop quality, and increased harvesting costs.

Over the years, synthetic chemical pesticides have provided an effective means of pest control. For example, one approach teaches the use of complex, organic insecticides, such as disclosed in U.S. Pat. Nos. 4,376,784 and 4,308,279. Other approaches employ absorbent organic polymers for widespread dehydration of the insects. See, U.S. Pat. Nos. 4,985,251; 4,983,390; 4,818,534; and 4,983,389. Use of inorganic salts as components of pesticides has also been tried, as disclosed in U.S. Pat. Nos. 2,423,284 and 4,948,013, European Patent Application No. 462 347, Chemical Abstracts 119(5):43357q (1993) and Farm Chemicals Handbook, page c102 (1987).

However, it has become increasingly apparent that the widespread use of synthetic chemical pesticides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Moreover, some target pests have even shown an ability to develop immunity to many commonly used synthetic chemical pesticides. In recent times, regulatory guidelines have encouraged a search for potentially less dangerous pesticidal compositions via stringent restrictions on the use of certain synthetic pesticides. As a result, elimination of effective pesticides from the market has limited economical and effective options for controlling pests. As an alternative, botanical pesticides are of great interest because they are natural pesticides, i.e., toxicants derived from plants that are safe to humans and the environment. Historically, botanical pesticides, such as tobacco, pyrethrum, derris, hellebore, quassia, camphor and turpentine, have long been used. Of the botanical pesticides, pyrethrum (also known as pyrethrum, caucasian pyrethrum, dalmatic pyrethrum, pesticide chrysanthemum, natural pyrethrum and pyrethrin) has found widespread use.

Pyrethrum, which is extracted from the flowers of a chrysanthemum grown in Kenya and Ecuador, acts on insects with phenomenal speed causing immediate paralysis, while at the same time exhibits negligible toxic effects on humans and warm-blooded animals. Use of pyrethrum for industrial or agricultural applications, however, is disadvantageous in that they require frequent treatments because they become volatile when in contact with water and readily decompose when exposed to direct sunlight light. Pyrethrums are also neurotoxic to cold-blooded animals, such as fishes, snakes, etc. Moreover, the supply of pyrethrums is limited and substantial processing is required to bring the natural product to market, and large-scale production of pyrethrum is very expensive and unless pyrethrum is formulated with a synergist, most initially paralyzed insects recover to once again become pests.

Synergists are compounds that, although typically possessing no direct toxic effect at the dosage employed, are able to substantially enhance the observed toxicity of a pesticide with which they are combined. Synergists are found in most all household, livestock and pet aerosols to enhance the action of the fast knockdown pesticides, e.g., pyrethrum, allethrin, and resmethrin, against flying insects. Synergists are required in pesticidal formulations containing pyrethrum, for example, because target insects produce an enzyme (cytochrome P-450) that attacks pyrethrum and breaks it down, thereby making it effective in knocking an insect down, but ineffective for killing in many cases. As such, these synergists act by inhibiting P-450 dependent polysubstrate monooxygenases enzymes (PSMOs) produced by microsomes, which are subcellular units found in the liver of mammals and in some insect tissues that degrade pyrethrum and other pesticidal compounds, such as pyrethrum, allethrin, resmethrin, and the like. These synergists inhibit P-450 enzymes and other like compounds that are part of the gene battery that comprise Phase I and Phase II drug metabolizing enzymes.

Because pyrethrum is limited in availability and is very expensive, the industry has turned to synthetic pyrethroids, which are very photostable in sunlight and are generally effective against most agricultural insect pests. Pyrethroids are not as safe as pyrethrums, however, and disadvantageously persist in the environment for longer periods. Further, many insects disadvantageously develop resistance to pyrethroids.

Many natural products used as insecticides, including plant essential oils, do not provide adequate control of pests in that they either act very slowly or are not very stable and break down quickly, thereby failing to provide quick knockdown of insects or toxic residual properties. Even products such as pyrethrum, although highly toxic to pests on contact when used properly in pesticidal formulations, are not effective pesticides for many applications because they lack residual properties, thereby increasing the frequency and cost of pesticide applications, as well as increased risk and exposure to the environment.

Accordingly, there is a great need for novel synergistic and residual pesticidal compositions containing no level or substantially lower levels of pyrethrum, chlorinated hydrocarbons, organo phosphates, carbamates and the like. In addition, there is a need for methods for using same that address the problems described above, i.e., are safe to humans and the environment and relatively inexpensive to use in obtaining acceptable levels of insect or pest control.

SUMMARY OF THE INVENTION

A primary object of the present invention is to provide novel pesticidal compositions that contain mixtures of one or more plant essential oils and/or derivatives thereof, natural or synthetic, with so-called Phase I and Phase II drug metabolizing enzyme inhibitors.

Another object of the invention is to provide pesticidal compositions containing synergistic mixtures or blends of plant essential oils and/or derivatives thereof, natural or synthetic, and other synergists with Phase I and Phase II drug metabolizing enzyme inhibitors.

A further object of the present invention is to provide novel, residual pesticidal compositions that contain admixtures of certain compounds, natural or synthetic, with one or more plant essential oils and/or derivatives thereof, natural or synthetic, that act to residualize the toxic effects of pesticidal compositions containing the plant essential oils.

It is also an object of the present invention to provide a pesticidal composition and method for mechanically, physiologically and/or neurally controlling pests, e.g., invertebrates, insects, arachnids, larvae thereof, etc.

It is a further object to provide a safe, non-toxic pesticidal composition and method that will not harm the environment.

It is still another object to provide a pesticidal composition and method that has a pleasant scent or is unscented, and that can be applied without burdensome safety precautions.

It is still another object to provide a pesticidal composition and method as described above which can be inexpensively produced or employed.

It is yet another object of the invention to provide a pesticidal composition and method to which pests cannot build immunity and/or resistance.

The above and other objects are accomplished by the present invention which is directed to synergistic and residual pesticidal compositions comprising plant essential oils and/or derivatives thereof, natural or synthetic, in admixture with Phase I and Phase II drug metabolizing enzyme inhibitors, or synergistic and residual pesticidal compositions comprising plant essential oils and Phase I and Phase II drug metabolizing enzyme inhibitors in admixture with other synergists. In addition, the present invention is directed to a method for controlling pests by applying a pesticidally-effective amount of the above synergistic and residual pesticidal compositions to a locus where pest control is desired.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety. In the case of inconsistencies, the present disclosure, including definitions, will prevail.

In one embodiment, the present invention provides a synergistic and residual pesticidal composition comprising, in admixture with a suitable carrier and optionally with a suitable surface active agent, comprising one or more plant essential oil compounds and derivatives thereof, natural or synthetic, including racemic mixtures, enantiomers, diastereomers, hydrates, salts, solvates and metabolites, etc. in admixture with an enzyme inhibitor, such as, for example, piperonyl butoxide (PBO), N-(2-ethylhexyl)-bicyclo-(2,2,1) hept-5-ene2,2-dicarboximide (MGK 264), and sesamex. In a preferred embodiment, the enzyme inhibitor is a P-450 enzyme inhibitor.

Each plant essential oil or derivative thereof, comprises a monocyclic, carbocyclic ring structure having six-members and substituted by at least one oxygenated or hydroxyl functional moiety. Examples of plant essential oils encompassed within the present invention, include, but are not limited to, members selected from the group consisting of aldehyde C16 (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, menthol, methyl anthranilate, methyl ionone, methyl salicylate, α-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like. As these plant essential oil compounds are known and used for other uses, they may be prepared by a skilled artisan by employing known methods.

For example, in a preferred embodiment, the present invention is directed to a synergistic pesticidal composition for controlling household pests comprising benzyl alcohol and piperonyl butoxide. Data below shows that this embodiment is highly effective, i.e., exhibited increased toxicity, against American cockroaches and carpenter ants compared to either the individual plant essential oil or piperonyl butoxide used alone.

In another embodiment, the present invention encompasses synergistic and residual pesticidal compositions comprising at least one of the above plant essential oil compounds with piperonyl butoxide, and a member selected from the group consisting of pyrethrolone, allethrolone, chrysanthemic acid, chrysanthemyl alcohol, chrysanthemate ester, cis-jasmone, tetrahydrofurfuryl alcohol (THFA), Lavendustin A (N-(2',5'-Dihydroxybenzyl)-N-(2''-hydroxybenzyl)-3-aminosalicylic Acid (CAS No.: 125697-92-9) ), and PD 98059, (2'-amino-3'-methoxyflavone), in admixture with a suitable carrier and optionally a suitable surface active agent.

It will be appreciated by the skilled artisan that the synergistic and residual pesticidal compositions of the present invention unexpectedly exhibit excellent pesticidal activities using one or more plant essential oils, in lieu of pyrethrum, in admixture with Phase I and Phase II drug metabolizing enzyme inhibitors such as piperonyl butoxide, MGK 264 and/or sesamex. Further, it will be appreciated by the skilled artisan that the synergistic and residual pesticidal compositions of the present invention unexpectedly exhibit pesticidal activity for extended periods of time, (i.e. using natural compounds as residual insecticides that in and of themselves provide little, if any, residual pesticidal properties). Without wishing to be bound by the following theories, it is believed that plant essential oils antagonize a pest's nerve receptors or may act as Phase I and/or Phase II drug metabolizing enzyme inhibitors themselves. Alternatively, plant essential oils may act via an alternative mode of action. Further, another possibility is that Phase I and/or Phase II drug metabolizing enzyme inhibitors synergize the plant essential oils, and may act to reduce the volatility of the natural compounds. The Phase I and/or Phase II drug metabolizing enzyme inhibitors may also increase energy levels within the insect's metabolism, thereby synergizing the antagonistic action of so-called octopamine affectors. In any event, the net effect of the increased toxicity and synergized action of the inventive synergistic composition disclosed herein is heretofore unknown and unexpected.

Use of synergistic and residual pesticidal compositions of the present invention generally results in 100% mortality on contact, and provides residual toxic properties for at least two weeks. As such, they are advantageously employed as pesticidal agents in uses such as, without limitation, agriculture, organic farming, households, professional pest control, pet bedding, foliage application, underwater or submerged application, solid treatment, soil incorporation application, seedling box treatment, stalk injection and planting treatment, ornamentals, termites, mosquitoes, fire ants, head lice, dust mites, etc.

With respect to plants, the synergistic and residual pesticidal compositions resist weathering which includes wash-off caused by rain, decomposition by ultra-violet light, oxidation, or hydrolysis in the presence of moisture or, at least such decomposition, oxidation and hydrolysis as would materially decrease the desirable pesticidal characteristic of the synergistic and residual compositions or impart undesirable characteristics to the synergistic and residual compositions. The synergistic and residual compositions are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

The term "carrier" as used herein means an inert or fluid material, which may be inorganic or organic and of synthetic or natural origin, with which the active compound is mixed or formulated to facilitate its application to the plant, seed, soil or other object to be treated, or its storage, transport and/or handling. In general, any of the materials customarily employed in formulating pesticides, herbicides, or fungicides, are suitable. The inventive synergistic and residual pesticidal compositions of the present invention may be employed alone or in the form of mixtures with such solid and/or liquid dispersible carrier vehicles and/or other known compatible active agents, especially plant protection agents, such as other pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The synergistic and residual pesticidal compositions of the present invention can be formulated or mixed with, if desired, conventional inert (i.e. plant compatible or herbicidally inert) pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

Formulations containing the synergistic and residual compositions of the present invention may be prepared in any known manner, for instance by extending the synergistic and residual compositions with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the synergistic and residual compositions of the present invention. Generally, it is desirable to use as little of the agent as is possible, consistent with the desired dispersion of the synergistic and residual compositions of the present invention in the spray so that rain does not re-emulsify the synergistic and residual compositions of the present invention after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

Liquid concentrates may be prepared by dissolving a composition of the present invention with a non-phytotoxic solvent and dispersing the synergistic and residual compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.).

Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which acts carriers for the pesticide. These finely divided solids preferably have an average particle size of less than about 50 microns. A typical dust formulation useful for controlling insects contains 1 part of synergistic and residual composition and 99 parts of diatomaceous earth or vermiculite. Granules may comprise porous or nonporous particles. The granule particles are relatively large, a diameter of about 400-2500 microns typically. The particles are either impregnated or coated with the inventive pesticidal compositions from solution. Granules generally contain 0.05-15%, preferably 0.5-5%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

If desired, volatile organic compounds suitable as the fragrance ingredient for use in formulations for household or pet applications, include, but are not limited to, amyl salicylate, citronellol, citronelloxyacetaldehyde, cyclamen aldehyde, citronellyl isobutyrate, coumarin, cyclohexyl acetate, cyclohexyl butyrate, diethyl malonate, ethyl 2-acetyl-5-ketohexanoate, isobornyl acetate, linalool, phenethyl alcohol, undecanol, alpha-hexylcinnamaldehyde, 2-methylhexanol, hexalon, phenylacetaldehyde, cis-3-hexen-1-ol, cyclamal, veronol, eugenol, Lyral, Galaxolide, Citralva, musk ambrette, terpinyl acetate, geraniol, alpha-damascone, alpha-methylionone, and the like. Illustrative of volatile essential oils are oil of Bergamot, cedar leaf, cedar wood, geranium, lavender, white cedar, sandalwood oil, rose extract, violet extract, galbanum oil, and the like. Synthetic types of organic fragrances are described in publications such as U.S. Pat. Nos. 4,314,915; 4,411,829; and 4,434,306.

In commercial or agricultural applications, the present invention encompasses carrier composition mixtures in which the synergistic and residual compositions are present in an amount substantially between about 0.01-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The synergistic and residual compositions can also be used in accordance with so-called ultra-low-volume process, i.e. by applying such compounds or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed. In this process it is possible to use highly concentrated liquid compositions with said liquid carrier vehicles containing from about 20 to 95% by weight of the synergistic and residual compositions or even the 100% active substances alone, e.g. about 20-100% by weight of the synergistic and residual compositions. The mixture of active materials may be applied, without limitation, in sufficient amounts so as to provide about 0.2 to 2 and preferably about 0.5 to 1.5 pounds of active materials per acre. Moreover, the required amount of the synergistic and residual composition contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to 90 percent by weight. Satisfactory sprays, dusts, or granules for general use contain from about ¼ to 15 pounds of active synergistic and residual compositions per acre.

Furthermore, the present invention encompasses methods for killing, combating or controlling pests, which comprises applying to at least one of correspondingly (a) such pests and (b) the corresponding habitat thereof, i.e. the locus to be protected, e.g. to a growing crop, to an area where a crop is to be grown or to a domestic animal, a correspondingly combative, a pesticidally effective amount, or toxic amount of the particular synergistic and residual compositions of the invention alone or together with a carrier as noted above. The instant formulations or compositions may be applied in any suitable usual manner, for instance by spraying, atomizing, vaporizing, scattering, dusting, watering, squirting, sprinkling, pouring, fumigating, and the like. The method for controlling insects comprises applying the inventive composition, ordinarily in a formulation of one of the aforementioned types, to a locus or area to be protected from the insects, such as the foliage and/or the fruit of plants. The compound, of course, is applied in an amount sufficient to effect the desired action. This dosage is dependent upon many factors, including the targeted pest, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage with which the pest comes in contact—is of the order of 0.001 to 5.0% based on the total weight of the formulation, though under some circumstances the effective concentration will be as little as 0.0001% or as much as 20%, on the same basis.

The synergistic and residual pesticidal compositions and methods of the present invention are effective against a wide variety of pests and it will be understood that the pests exemplified and evaluated in the working Examples herein is representative of such a wider variety. For instance, the present invention can be used to control pests that attack plants or warm-blooded animals, stored products and fabrics. Representative crop plants that can be so treated include, without limitation, are cotton, corn, deciduous and citrus fruits, tomatoes, maize, ornamental plants potatoes, rice, soybean, sugar beets, tobacco, wheat, etc. Representative animals that can be protected or treated by the present invention include, without limitation, man, horses, dogs, cats, cattle, sheep, goats, hogs, etc. Representative stored products that can be protected from pest attack by the present invention include, without limitation, grains, flour and flour products, tobacco and tobacco products, processed foods, cereals and the like. Representative fabrics that can be protected from pest attack by the invention are wool, cotton, silk, linen and the like.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE 1

Synergistic and Residual Effects of Plant Essential Oils and Piperonyl Butoxide on the American Cockroach Plant essential oils, alone and in combination with piperonyl butoxide (PBO), were evaluated for synergistic and residual toxicity against American cockroaches. Glass jars were treated with different concentrations of the materials diluted in acetone solvent. The treated jars were left uncovered for approximately one hour so that the acetone would evaporate, and then the insects were introduced into the jars at different intervals after jar treatment. Insect mortality was observed after 24 hour exposure to the treated jars. Five cockroaches were used for each cross-walk treatment. Two replicates/treatment. This experiment was repeated 3 times.

| No. | Test Chemical* | % Mortality (days after treatment) | | | | | | | |
|---|---|---|---|---|---|---|---|---|---|
| | | 1 hr | 7 | 14 | 21 | 28 | 35 | 45 | 50 |
| 1 | Control (100) | 0 | 0 | 0 | 0 | 0 | 0 | 0 | 0 |
| 2 | PBO (100) | 80 | 50 | 30 | 0 | 0 | 0 | 0 | 0 |
| 3 | PBO (100) + BA (100) + C-ester (25) | 100 | 100 | 100 | 100 | 20 | 0 | 0 | 0 |
| 4 | PBO (100) + C-ester (25) | 100 | 100 | 90 | 80 | 70 | 0 | 0 | 0 |
| 5 | PBO (100) + BA (100) | 100 | 70 | 50 | 0 | 0 | 0 | 0 | 0 |
| 6 | PBO (100) + BA (50) | 100 | 100 | 100 | 100 | 70 | 0 | 0 | 0 |
| 7 | PBO (100) + C-acid (25) | 100 | 70 | 70 | 90 | 100 | 50 | 40 | 0 |
| 8 | PBO (100) + C-alcohol (25) | 100 | 80 | 70 | 80 | 100 | 50 | 40 | 40 |
| 9 | PBO (30) + thymol (30) | 100 | 60 | 60 | 70 | 80 | 80 | 80 | 0 |
| 10 | PBO (100) + eugenol (500) | 100 | 100 | 100 | 0 | 0 | 0 | 0 | 0 |

*Measured in mg/jar of test substance
BA = Benzyl Alcohol
C-Ester = Chrysanthemate ester
C-Acid = Chrysanthemic acid
C-Alcohol = Chrysanthemyl alcohol These examples show the synergistic properties of plant essential oils combined with enzyme inhibitors such as PBO, along with other synergists not expected to act as enzyme inhibitors. The data clearly shows synergistic action, as well as strong residual toxicity for almost two months with certain mixtures. The data also demonstrates that the ratio of the items in the mixture is an important factor in the resulting synergy and residual toxicity. For example, a 1:1 mixture of PBO to benzyl alcohol did not produce synergistic properties whereas a 2:1 mixture of the same compounds respectively gave synergistic action and provided four weeks residual toxicity. In contrast, PBO and thymol at 1:1 ratio produced synergistic properties and provided residual toxicity for more than a month. These data are unanticipated and demonstrate the synergistic action among these compounds.

EXAMPLE 2

Synergistic Action of Piperonyl Butoxide on Plant Essential Oils with other Synergists Against the American Cockroach Plant essential oils, in combination with piperonyl butoxide (PBO) and/or other synergists, were evaluated for synergistic and residual toxicity against American cockroaches. Glass jars were treated with different concentrations of the materials diluted in acetone solvent. The treated jars were left uncovered for approximately one hour so that the acetone would evaporate, and then the insects were introduced into the jars at different intervals after jar treatment. Insect mortality was observed after 24 hour exposure to the treated jars. Five cockroaches were used for each cross-walk treatment. Two replicates/treatment. This experiment was repeated 3 times.

| No. | Test Chemical* | % Mortality (days after treatment) | | | | |
|---|---|---|---|---|---|---|
| | | 1 hr | 7 | 14 | 21 | 28 |
| 11 | Control (100) | 0 | 0 | 0 | 0 | 0 |
| 12 | BA (50) + PBO (100) + C-acid (25) | 100 | 100 | 100 | 80 | 60 |
| 13 | BA (25) + PBO (100) + C-acid (25) | 100 | 100 | 100 | 100 | 100 |
| 14 | BA (50) + PBO (100) + C-alcohol (25) | 100 | 100 | 100 | 0 | 0 |
| 15 | BA (25) + PBO (100) + C-alcohol (25) | 100 | 100 | 100 | 50 | 0 |
| 16 | BA (50) + C-ester (25) + PBO (100) | 100 | 100 | 100 | 60 | 60 |
| 17 | BA (25) + C-ester (25) + PBO (100) | 100 | 100 | 100 | 60 | 40 |
| 18 | BA (25) + PBO (100) + C-acid (12.5) + C-alcohol (12.5) | 100 | 100 | 100 | 100 | 60 |
| 19 | Eugenol (50) + PBO (100) | 100 | 100 | 100 | 100 | 60 |
| 20 | Eugenol (50) + PBO (100) + FK (0.1) | 100 | 100 | 100 | 100 | 100 |

*Measured in mg/jar of test substance
BA = Benzyl Alcohol
C-Ester = Chrysanthemate ester
C-Acid = Chrysanthemic acid
C-Alcohol = Chrysanthemyl alcohol
FK = Forskolin These data clearly show the synergized action of the mixtures, even at very low dosage rates and exposure levels. The test chemicals by themselves are not totally effective on contact at these levels and they certainly do not provide the unexpected residual toxicity without the enzyme inhibitors and synergists. Again, ratios are important in creating synergistic blends of these compounds. In Example 2, PBO:eugenol at 1:5 did not produce residual toxicity beyond 14 days, whereas PBO:eugenol at 2:1 provided residual toxicity for one month. Also, the addition of other synergists to the mixture, even at very low levels, appears to enhance the knockdown and residual toxicity of the mixtures. The resulting synergistic action from these low levels of synergists is clearly unexpected, especially since these synergists are not toxic to insects when used alone.

As can be seen from the above discussion, the synergistic and residual combinations of active compounds according to the present invention are markedly superior to plant essential oils and known pesticidal agents/active compounds conventionally used for pest control in the household and agricultural crops. The pesticidal effectiveness of the particular new synergistic and residual combinations of active compounds of the present invention is substantially (and surprisingly) higher than the sum of the separate effects of the individual active compounds.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A pesticidal composition comprising:
   an inert carrier and
   a pesticidally-effective active ingredient consisting of piperonyl butoxide and phenyl ethyl propionate,
   with the proviso that no other pesticidally-effective active ingredient is present.

2. The pesticidal composition of claim 1, wherein the piperonyl butoxide and phenyl ethyl propionate are present in a ratio of about 1:2 parts by weight.

3. A method for killing or controlling a pest, comprising:
   applying to a locus where killing or control of pests is desired a pesticidal composition comprising
   an inert carrier and
   a pesticidally-effective active ingredient consisting of piperonyl butoxide and phenyl ethyl propionate,
   with the proviso that no other pesticidally-effective active ingredient is present.

4. The method of claim 3, wherein the pest is a cockroach.

5. The method of claim 3, wherein the piperonyl butoxide and phenyl ethyl propionate are present in a ratio of about 1:2 parts by weight.

* * * * *